(12) United States Patent
Li et al.

(10) Patent No.: US 11,452,853 B2
(45) Date of Patent: Sep. 27, 2022

(54) MICRONEEDLE CHIP AND MANUFACTURING METHOD THEREOF

(71) Applicants: GUANGZHOU MICNANO BIOTECH CO., LTD, Guangdong (CN); GUANGZHOU NOVAKEN PHARMACEUTICAL CO., LTD., Guangzhou (CN)

(72) Inventors: Ge Li, Guangdong (CN); Hangping Chen, Guangdong (CN); Minmin Zhang, Guangdong (CN); Qian Zhang, Guangdong (CN); Gangtao Yao, Guangdong (CN)

(73) Assignees: GUANGZHOU MICNANO BIOTECH CO., LTD, Guangdong (CN); GUANGZHOU NOVAKEN PHARMACEUTICAL CO., LTD., Guangzhou (CN)

( * ) Notice: Subject to any disclaimer, the term of this patent is extended or adjusted under 35 U.S.C. 154(b) by 910 days.

(21) Appl. No.: 16/065,592

(22) PCT Filed: Jun. 21, 2016

(86) PCT No.: PCT/CN2016/086496
§ 371 (c)(1),
(2) Date: Jun. 22, 2018

(87) PCT Pub. No.: WO2017/107417
PCT Pub. Date: Jun. 29, 2017

(65) Prior Publication Data
US 2020/0197679 A1    Jun. 25, 2020

(30) Foreign Application Priority Data
Dec. 24, 2015 (CN) .......................... 201510998598.2

(51) Int. Cl.
*B29C 33/10* (2006.01)
*A61M 37/00* (2006.01)
(Continued)

(52) U.S. Cl.
CPC ......... *A61M 37/0015* (2013.01); *B29C 33/10* (2013.01); *B29C 33/3842* (2013.01);
(Continued)

(58) Field of Classification Search
None
See application file for complete search history.

(56) References Cited

U.S. PATENT DOCUMENTS

| 2009/0182306 A1 | 7/2009 | Lee et al. |
| 2009/0234301 A1* | 9/2009 | Tomono ................ B29C 43/021 604/272 |

(Continued)

FOREIGN PATENT DOCUMENTS

| CN | 102202723 A | 9/2011 |
| CN | 103301092 A | 9/2013 |

(Continued)

OTHER PUBLICATIONS

International Search Report and Written Opinion for International Application No. PCT/CN2016/086496 dated Aug. 29, 2016.

*Primary Examiner* — Jacob T Minskey
*Assistant Examiner* — Adrien J Bernard
(74) *Attorney, Agent, or Firm* — Dorsey & Whitney LLP (57) ABSTRACT

A microneedle chip and manufacturing method. The method comprises injecting, into a female mold, a fluid needle liquid, wherein forming cavities matching the shapes of needles of a microneedle chip are provided at the female mold and form a cavity array, injection inlets are provided at a surface of one side of the female mold, and air ejection openings are provided at a surface of another side of the (Continued)

female mold to form an air ejection surface; covering the air ejection surface of the female mold using a breathable film, and during injection, passing a gas through the breathable film so as to retain the liquid inside the forming cavities; curing the fluid needle liquid to form the microneedle chip, and demolding to obtain the same. By employing the air ejection openings and the breathable film, a liquid is retained while ejecting a gas, providing a favorable micro-injection effect.

11 Claims, 5 Drawing Sheets

(51) Int. Cl.
<table><tr><td>B29C 33/38</td><td>(2006.01)</td></tr><tr><td>B29C 45/00</td><td>(2006.01)</td></tr><tr><td>B29C 45/26</td><td>(2006.01)</td></tr><tr><td>B29C 45/34</td><td>(2006.01)</td></tr><tr><td>B29K 105/00</td><td>(2006.01)</td></tr><tr><td>B29L 31/00</td><td>(2006.01)</td></tr></table>

(52) U.S. Cl.
CPC ........ *B29C 45/0053* (2013.01); *B29C 45/263* (2013.01); *B29C 45/2626* (2013.01); *B29C 45/345* (2013.01); *A61M 2037/0053* (2013.01); *A61M 2205/0244* (2013.01); *A61M 2210/04* (2013.01); *B29C 2045/0079* (2013.01); *B29C 2045/2651* (2013.01); *B29K 2005/00* (2013.01); *B29K 2039/06* (2013.01); *B29K 2105/0035* (2013.01); *B29K 2827/18* (2013.01); *B29K 2867/00* (2013.01); *B29K 2883/00* (2013.01); *B29L 2031/7544* (2013.01)

(56) References Cited

U.S. PATENT DOCUMENTS

<table><tr><td>2011/0060274 A1*</td><td>3/2011</td><td>Kuhn</td><td>A61M 5/385<br>604/82</td></tr><tr><td>2012/0041337 A1*</td><td>2/2012</td><td>Ferguson</td><td>A61M 37/0015<br>600/573</td></tr><tr><td>2015/0238434 A1*</td><td>8/2015</td><td>Yoshida</td><td>A61K 38/27<br>424/443</td></tr><tr><td>2016/0136408 A1*</td><td>5/2016</td><td>Kato</td><td>B29C 39/003<br>604/173</td></tr><tr><td>2018/0021437 A1*</td><td>1/2018</td><td>Kim</td><td>A61M 37/00<br>514/777</td></tr></table>

FOREIGN PATENT DOCUMENTS

<table><tr><td>CN</td><td>104027324 A</td><td></td><td>9/2014</td><td></td></tr><tr><td>CN</td><td>104069585 A</td><td></td><td>10/2014</td><td></td></tr><tr><td>CN</td><td>104780968 A</td><td>*</td><td>7/2015</td><td>............ A61Q 19/08</td></tr><tr><td>CN</td><td>104780968 A</td><td></td><td>7/2015</td><td></td></tr><tr><td>CN</td><td>105498082 A</td><td></td><td>4/2016</td><td></td></tr><tr><td>CN</td><td>105643839 A</td><td></td><td>6/2016</td><td></td></tr><tr><td>JP</td><td>2015116335 A</td><td></td><td>6/2015</td><td></td></tr><tr><td>WO</td><td>2008010681 A1</td><td></td><td>1/2008</td><td></td></tr><tr><td>WO</td><td>2012023044 A1</td><td></td><td>2/2012</td><td></td></tr><tr><td>WO</td><td>2015010599 A1</td><td></td><td>1/2015</td><td></td></tr><tr><td>WO</td><td>WO-2015010599 A1</td><td>*</td><td>1/2015</td><td>............ B29C 69/00</td></tr></table>

\* cited by examiner

MICRONEEDLE CHIP AND MANUFACTURING METHOD THEREOF

TECHNICAL FIELD

The present disclosure relates to the technical field of transdermal administrating formulation, particularly to a microneedle chip and a manufacturing method thereof.

BACKGROUND

The microneedle transdermal administrating technology is a novel method for transdermal administration. The silicon and silicon oxide microneedles were initially used. Such microneedles have a mature manufacturing process, but disadvantages of poor biocompatibility, brittle quality, low productive rate, and the like, limiting its industrialization. Another type is metal microneedles. Such microneedles have a good mechanical strength, but disadvantages of small drug loading capacity, complicated process, high processing cost, also limiting the industrial production and clinical application of such microneedles.

A soluble microneedle refers to those having a needle body formed of dissolvable or degradable excipients, with which drug components is mixed, directly stored in the needle body, and release after the needle body penetrates into the skin. Currently, it is still difficult to achieve mass production in the manufacture of such microneedle due to its small size (with an operable space within 1 mm$^3$).

At this stage, the methods for manufacturing a soluble microneedle reported in the literatures, which are still in the laboratory stage, can be divided into two types: one method is to manufacture the soluble microneedle by dissolving a polymer material into water or ethanol, and by utilizing the viscosity of this solution, sandwiching and wire-drawing a small droplet of this solution between two plates (for example, WO 2008/010681A1). This method has the disadvantages of long time for production, precise control of the wire-drawing process, irregularly shaped needle bodies, formation of a needle body with a large base portion and a fine needle tip, easy breakage, slow industrial production rate, and poor controllability of production, and the like. Therefore, the soluble microneedle is still hard to realize in the pharmaceutical industry that must precisely control the dosage of drugs, but can be only used in the cosmetics industry.

The other method is to adopt a female mold microinjection to manufacture a soluble microneedle, the key step of which is to rapidly inject a flowing needle body material into a micropore; however, how to achieve an effective and rapid microinjection has become a crucial issue during the industrialization of the soluble microneedle. US patent No. US2009/0182306A1 and international patent publication No. WO2012/023044A1 propose to achieve a microinjection by the centrifugation or vacuum processes. However, it is difficult to achieve industrial production by the centrifugation process. Meanwhile, the process of vacuum depressurization or pressurization of 2 to 5 atmospheric pressures in a sealed container (as disclosed by Chinese patent No. CN104027324A) has a high requirement for the viscosity of solution used in the microinjection, and the viscosity should be controlled within 100 centipoise (cP); if the viscosity is higher, the solution will easily form an air embolism during the microinjection, leaving an incomplete injection. However, it is not true that the lower the viscosity is, the better the microinjection will be. For example, the drug such as vaccine, which requires only a dosage at nanogram level, must use other matrix as a filling material to achieve a physical strength and appearance required by transdermal administration. The solid content of the needle body solution has a certain correlation with the viscosity. In general, the higher the solid content is, the higher the viscosity will be; after drying, the needle body has small volume shrinkage. Therefore, a high-viscosity needle body solution is essential for the micro-injection. In the literatures, Rebecca E. M. Lutton and Sixing Yang et al. propose to use an extrusion or suction filtration process, wherein a mold used in the extrusion process must have the characteristics of good toughness, and whether the mold can fully recover after the needle hole is deformed under external force remains to be investigated. The key lies in that it is still hard to ensure that the liquid with high viscosity can be completely squeezed into each needle hole. Meanwhile, regarding the manufacture of soluble microneedles by suction filtration of the purple sand mold, whether the gas permeability of the mold is good or bad is a key issue in the production. Moreover, the mold of purple sand materials has a complicated manufacturing process, a calcination temperature as high as 1000° C., a tedious calcination process for over 15 hours, and also large energy consumption. Therefore, the industrialization is costly.

Thus, there is an urgent need to develop a method for manufacturing soluble microneedles that not only can be achieved in the laboratory, but also can be used in large-scale production.

SUMMARY

Based on this, in view of the above problems, it is necessary to provide a method for manufacturing a microneedle chip; the manufacturing method can be adapted to industrial production, and a microneedle chip obtained by the manufacturing method has a good quality.

A method for manufacturing a microneedle chip comprises the following steps:

Injecting a fluidized needle body liquid into a female mold, the fluidized needle body liquid containing a bioactive component, wherein the female mold is provided with a plurality of mold cavities matched with the shape of a needle body in the microneedle chip, each of the mold cavities is provided with an injecting inlet and an exhaust port, and the plurality of mold cavities are arranged in the same direction to form an array of mold cavities, and wherein the injecting inlet is open at one side surface of the female mold and located at a needle base end of the mold cavities, the exhaust port is open at the other side surface of the female mold and located at a needle tip end of the mold cavities, and a surface of the female mold having a plurality of the exhaust ports forms an exhaust surface;

passing gas through a gas-permeable membrane and retaining the liquid within the mold cavities when the exhaust surface of the female mold is covered with the gas-permeable membrane and the fluidized needle body liquid is injected;

demoulding after the fluidized needle body liquid is cured and the microneedle chip is formed.

The above method for manufacturing a microneedle chip is used for manufacturing a microneedle chip comprising a needle base layer and a needle body, a plurality of the needle bodies being arranged in a form of array on the needle base layer. When the microinjection is performed with the fluidized needle body liquid, the gas in the mold cavities of the female mold is expelled through the exhaust port, so that the fluidized needle body liquid can be rapidly injected into a tiny micropore of the mold cavities; then, by combining with the gas-permeable membrane having a waterproof and breathable function, the fluidized needle body liquid can be retained so as to keep in the micropore of the mold cavities matched with the shape of the needle body of the microneedle chip while expelling gas smoothly through the gas-permeable, and after the fluidized needle body liquid is cured and demoulded, the microneedle chip therefore can be obtained.

In addition, since the exhaust port is combined with the gas-permeable membrane, gas can be expelled while retaining liquid. Therefore, even if the fluidized needle body liquid has a high viscosity, no air embolism is formed during the microinjection, resulting in a good microinjection process.

In one embodiment, when the fluidized needle body liquid is injected into the female mold, a positive pressure is applied at a injecting side of the female mold to promote the injection of the fluidized needle body liquid into the mold cavities; and/or a negative pressure is formed by vacuumizing at an exhaust port side of the female mold to promote the injection of the fluidized needle body liquid into the mold cavities. By applying a positive pressure and/or a negative pressure, the microinjection effect of the fluidized needle body liquid can be improved.

In one embodiment, the positive pressure applied at the injecting side of the female mold has an intensity of pressure in the range of 0.001 Mpa to 0.9 Mpa, and the negative pressure formed by vacuumizing at the exhaust port side of the female mold has an intensity of pressure in the range of −0.9 Mpa to −0.001 Mpa. A better microinjection effect can be achieved with only a low pressure within the above range, which has the advantage of strong operability in the industrial production.

In one embodiment, the fluidized needle body liquid has a viscosity in the range of 100 cps to 60,000 cps. The manufacturing method is suitable for a fluidized needle body liquid having a wide range of viscosity and has a good applicability.

In one embodiment, the fluidized needle body liquid has a viscosity in the range of 2,000 cps to 40,000 cps. The fluidized needle body liquid within the above range has the advantages of good microinjection effect and a small amount of shrinkage after the needle body of the microneedle chip is cured.

In one embodiment, the female mold includes a main body portion and a base portion; the main body portion is provided with the plurality of the mold cavities, the injecting inlet at one side surface and the exhaust port at the other side surface, and the exhaust surface is formed by a surface provided with the exhaust port; the base portion has an inner surface covering over the exhaust surface and is internally provided with an exhaust hole, the exhaust hole being in communication with the exhaust port at an end and open at an outer surface of the base portion at the other end, and having the same maximum radial size as that of the exhaust port and a length greater than 0 μm but less than or equal to 500 μm; and the gas-permeable membrane covers over the outer surface of the base portion. The above main body portion and the base portion are integrally molded to form a one-piece female mold. The demoulding will be easier and the content of the bioactive component of the needle body can be more easily controlled as the exhaust hole makes a shorter hole channel. Meanwhile, the longer the hole channel of the exhaust hole is, the greater the resistance will be, which is detrimental to micro-injection.

In one embodiment, the female mold has a thickness from an injecting inlet side to an outer surface side of the base portion in the range of 50 μm to 3,000 μm. The female mold having an overall thickness within the above range not only can satisfy the requirement for the manufacture of the microneedle, but also can be distinguished from the conventional needles for injection, and the effect of being painless or slightly painful from microneedle can be achieved.

In one embodiment, the exhaust port has a pore size in the range of 0.1 μm to 100 μm, preferably, in the range of 15 μm to 50 μm. It can be understood that if the exhaust port is round in shape, the diameter is the maximum radial size; if the exhaust port is square in shape, the diagonal line length is the maximum radial size. If the exhaust port has a small pore size, the gas will not be expelled smoothly during microinjection, while if the exhaust port has a large pore size, the injection will be adversely affected, and the needle tip of the microneedle chip manufactured will be too thick and affects its performance for inserting into the skin. By limiting the pore size of the exhaust port within the above range, it not only allows to ensure the smoothness of gas exhaust, but also to guarantee the smooth progress of the injection; when the microneedle chip is demoulded, it allows to guarantee the smooth demoulding of the microneedle, so as to obtain a microneedle chip with a shape that satisfying the requirement.

In one embodiment, the gas-permeable membrane is waterproof and has a gas permeability in the range of 120 to 1,500 $cm^3/(cm^2/h)@0.1$ bar under a positive pressure in the range of 0.001 Mpa to 0.5 MPa, or under a negative pressure in the range of −0.5Mpa to −0.001 Mpa. The gas permeability indicates that the gas-permeable membrane has a gas permeability of 120 to 1,500 $cm^3$ at per 1 $cm^2$ area for 1 hour under a pressure of 0.1 bar. The gas-permeable membrane needs to satisfy the above requirement in order to have a good waterproof and breathable function when a pressure is applied during micro-injection.

In one embodiment, the gas-permeable membrane is made of a polytetrafluoroethylene film or an adhesive fiber membrane of polytetrafluoroethylene and polyester fiber, wherein the polytetrafluoroethylene film further includes an expanded polytetrafluoroethylene film. The gas-permeable membrane is preferably an adhesive film of expanded polytetrafluoroethylene and expanded polyester fiber. By using the above material, the gas-permeable membrane has a good waterproof and breathable function.

In one embodiment, the female mold is made of polydimethylsiloxane. The female mold is preferably made of Sylgard 184 silicone elastomer or SILASTIC MDX4-4210 silicone elastomer. The female mold made of the above material will not cause the breakage of the needle body during demoulding due to a poor quality of the female mold, and can be well demoulded to give a complete microneedle chip.

Among them, Sylgard 184 silicone elastomer is dimethylvinylsiloxane-terminated dimethylsiloxane, dimethylvinylated silica, and trimethylsilylated silica, comprises a curing agent containing dimethylvinylsiloxane-terminated dimethylsiloxane, trimethylsiloxane-terminated dimethylmethylhydridosiloxane, dimethylvinylated silica, and trimethylsilylated silica.

SILASTIC MD X4-4210 silicone elastomer is a biopharmaceutical-grade silicone elastomer containing dimethylvinylsiloxane-terminated dimethylsiloxane and silica silylate, and comprises a curing agent containing dimethylvinylsiloxy-terminated dimethylsiloxane, and trimethylsiloxane-terminated dimethylmethylhydridosiloxane.

In one embodiment, after the fluidized needle body liquid is injected into the mold cavities of the female mold, a needle base material is coated on a needle base portion of the microneedle chip by means of coating, and the fluidized needle body liquid and the needle base material, after being cured, are demoulded to give a microneedle chip. Preferably, a membrane coated has a thickness in the range of 25 µm to 4,000 µm. In addition, preferably, excess fluidized needle body liquid outside the mold cavities is firstly scraped away after the fluidized needle body liquid is injected into the mold cavities of the female mold, and then the needle base material is coated on the needle body base of the microneedle chip by means of coating.

In one embodiment, the needle base material is at least one of polyvinylpyrrolidone, copolymer Gantrez AN-139, copolymer Gantrez S97 BF, and hyaluronic acid.

The present disclosure further discloses a microneedle chip manufactured according to the above method for manufacturing a microneedle chip.

The microneedle chip obtained by using the above manufacturing method has the advantages of a good uniformity and quality due to a good micro-injection effect and no air embolism formation during the microinjection, i.e., less prone to phenomenon of needle breakage or deficiency.

The above female mold can be made by the following method:

Firstly, manufacturing a male mold with a microneedle chip needle body model; injecting a female mold liquid solution into the above resulted male mold; curing; and demoulding, so as to give a female mold provided with an exhaust port in mold cavities.

By combining the female mold liquid solution with a male mold, a female mold provided with a tiny vent hole can be made. In the above male mold, the microneedle chip needle body model has a height in the range of 150 µm to 2,000 µm, a bottom diameter in the range of 100 µm to 500 µm, and a tip diameter of less than or equal to 50 µm.

In one embodiment, the female mold is obtained by the following steps: placing the male mold provided with an array of microneedle chip with the needle tip facing upward after the male mold with the microneedle chip needle body model is made; then injecting the female mold liquid solution into the male mold resulted from the above step; piercing a liquid surface of the female mold liquid solution with the needle tip of the microneedle chip in the male mold; contacting the needle tip with air to form an exhaust port; curing; and demoulding.

Alternatively, the female mold is obtained by the following steps: placing the male mold with the needle tip facing upward after the male mold with a microneedle chip needle body model is made; then injecting the female mold liquid solution into the male mold resulted from the above step so that the needle tip of the microneedle chip in the male mold is immersed into the female mold liquid solution; curing; demoulding so as to give a female mold provided with a needle hole at one side; and then perforating at a position corresponding to the needle hole at the other side of the female mold to form an exhaust port.

Alternatively, the female mold is obtained by the following steps: injecting a liquid solidifying solution into a container after the male mold with a microneedle chip needle body model is made; then placing the male mold on the container with the needle tip facing downwards so that the needle tip is inserted under a liquid surface of the solidifying solution; injecting the female mold liquid solution into the container after the solidifying solution is cured, so that a hollow chamber between the solidifying solution and the male mold is filled up with the female mold liquid solution; and demoulding after the female mold liquid solution is cured.

In one embodiment, the male mold comprises a substrate, an array of microneedle chip needle body model and a side plate. The array of microneedle chip needle body model is provided on the substrate, the substrate being provided with a pore for injecting a liquid; the side plate is cooperated with a side wall of the container, so that an opening of the container is closed with the male mold; and a fine adjusting knob for adjusting the height for placing the male mold is provided at a juncture between the side plate and the side wall of the container.

The above female mold can also be made by the following method:

placing the female mold liquid solution into the container; curing; demoulding so as to give a female mold without mold cavities; and then perforating the female mold to make mold cavities and an exhaust port so as to give the female mold.

Compared with the existing technology, the present disclosure has the following beneficial effects:

according to the method for manufacturing a microneedle chip of the present disclosure, when the fluidized needle body liquid is injected, the gas in the mold cavities of the female mold is expelled through the exhaust port, so that the fluidized needle body liquid can be rapidly injected into a tiny micropore of the mold cavities; then, by combining with the gas-permeable membrane having a waterproof and breathable function, the fluidized needle body liquid can be retained so as to keep in the micropore of the mold cavities matched with the shape of the needle body of the microneedle chip while passing gas smoothly through the gas-permeable; and after the fluidized needle body liquid is cured and demoulded, the microneedle chip therefore can be obtained.

In addition, since the exhaust port is combined with the gas-permeable membrane, gas can be expelled while retaining liquid. Therefore, even if the fluidized needle body liquid has a high viscosity, no air embolism is formed during the microinjection, resulting in a good microinjection effect.

In a process flow of the manufacturing method, it is not necessary to perform processes that are difficult to realize in industrial production, such as centrifugation, and the like, or to use technical means with high industrialization cost, such as applying a high pressure, applying a high temperature, and the like. The manufacturing method has the advantages of simplicity, feasibility, and low cost, and is suitable for promotional use in industrialization.

In addition, the manufacturing method, in which the exhaust port and exhaust hole is screened and optimized for shape and size and the best setting modes for the exhaust port and the exhaust hole are found, can guarantee not only a smooth gas exhaust but also no microneedle material of portions (exhaust port and exhaust hole) left at the needle tip of the microneedle chip.

In the manufacturing method, the gas-permeable membrane is further screened and optimized for material, and the material specification of the gas-permeable membrane that is optimally matched with the exhaust port are found, further enhancing the operability of manufacturing method.

The microneedle chip obtained by using the above manufacturing method, due to a good microinjection effect and no air embolism formation during the microinjection, i.e., less prone to phenomenon of needle breakage or deficiency, has a better uniformity and quality than those manufactured by conventional methods.

BRIEF DESCRIPTION OF THE DRAWINGS

wherein: 100. male mold; 200. female mold; 210. main body portion; 211. exhaust port; 212. injecting inlet; 220. base portion; 221. exhaust hole; 300. gas-permeable membrane; 410. supporting plate; 420. vacuum pump; 430. first frame body; 500. second frame body; 510. liquid loading port; 600. fluidized needle body liquid; 610. needle body; 700. needle base material; 710. needle base layer.

DETAILED DESCRIPTION OF EMBODIMENTS

To facilitate the understanding of the present disclosure, the present disclosure will be described more fully hereinafter with reference to the accompanying drawings. The accompanying drawings show preferred embodiments of the present disclosure. However, the present disclosure may be embodied in many different forms and is not limited to the embodiments described herein. Rather, these embodiments are provided for a purpose of more thorough and full understanding of the present disclosure.

It should be noted that when an element is considered as being "in communication with" another element, it can be communicated with an element directly or a mediating element may be also present.

Unless otherwise specified, all technical and scientific terms used herein have the same meaning as commonly understood by one of ordinary skill in the art to which the present disclosure belongs. The terms used herein is for the purpose of describing specific example only and is not intended to limit the present disclosure. As used herein, the term "and/or" includes any and all combinations of one or more of the associated items listed.

Each of the raw materials used in the following examples are as follows:

Sylgard 184 silicone elastomer, model Sylgard® 184, purchased from Dow Corning Corporation (USA);

SILASTIC MDX4-4210 silicone elastomer of biomedical grade, model Silastic MDX4-4210, purchased from Dow Corning Corporation (USA);

adhesive film of polytetrafluoroethylene and polyester fiber, model PUW876, purchased from DONG GUAN PUW EPTFE MATERIAL CO., LTD.;

expanded polytetrafluoroethylene film, model PUW576, purchased from DONG GUAN PUW EPTFE MATERIAL CO., LTD.;

Polyvinylpyrrolidone (PVP) K30, model K30, purchased from BASF (Germany);

Copolymer Gantrez AN-139, model Gantrez AN-139, purchased from Ashland (USA);

Copolymer Gantrez S97 BF, model Gantrez S97 BF, purchased from Ashland (USA).

The mold used in the following examples is as follows:

A mold for manufacturing a microneedle chip comprises a female mold and a gas-permeable membrane.

Figure 1:
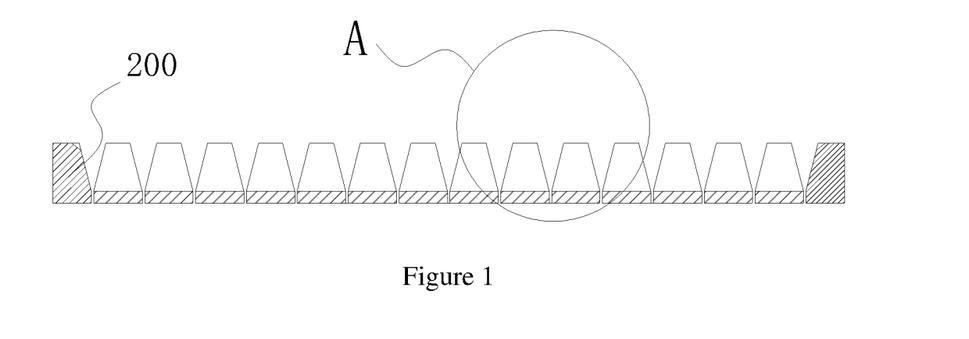
FIG. 1 is a cross-sectional schematic view of a female mold according to a specific embodiment.
Figure 2:
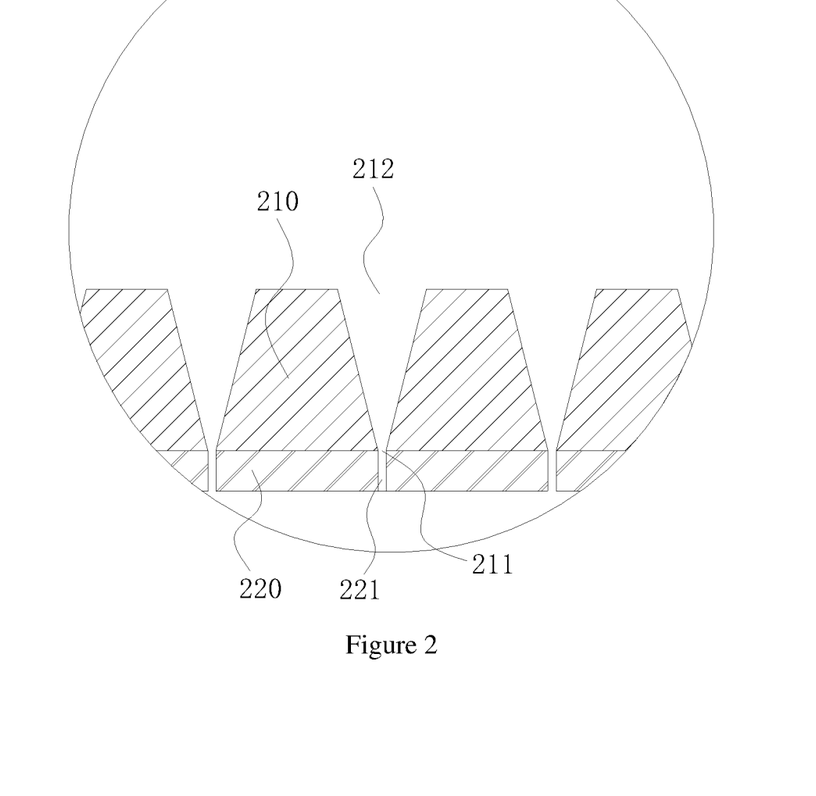
FIG. 2 is an enlarged schematic view of part A shown in FIG. 1.

As shown in FIGS. 1-2, a female mold 200 is provided with a plurality of mold cavities matched with the shape of a needle body of the microneedle chip, each of the mold cavities is provided with an injecting inlet 212 and exhaust port 211, and the plurality of mold cavities are arranged in the same direction to form an array of mold cavities; the injecting inlet 212 is open at one side surface of the female mold and located at a needle base end of the mold cavities, the exhaust port 212 is open at the other side surface of the female mold and located at a needle tip end of the mold cavities, and a surface of the female mold having a plurality of the exhaust port 211 forms an exhaust surface.

Figure 3:
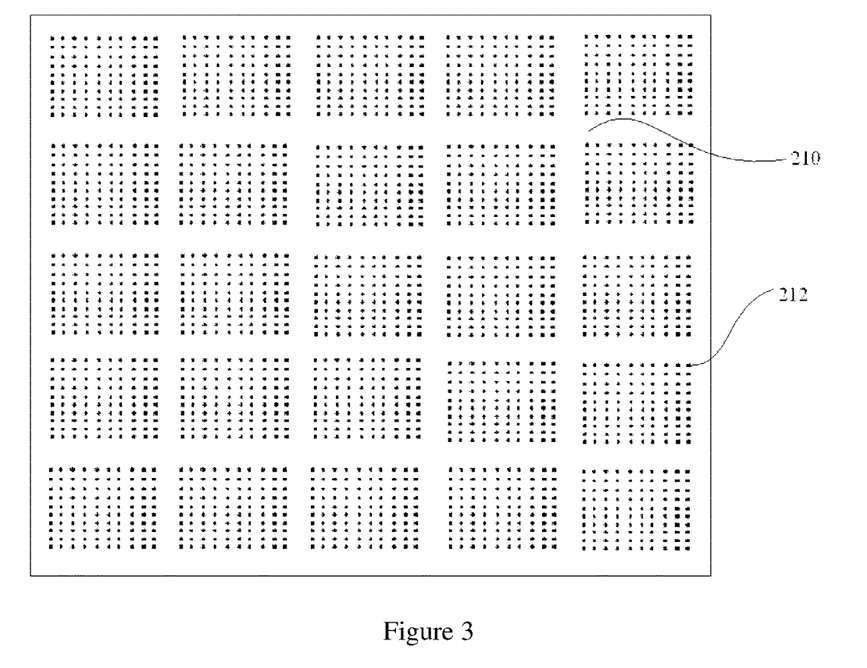
FIG. 3 is a top schematic view of a female mold according to a specific embodiment.

In some embodiments, as shown in FIG. 2, the female mold is divided into a main body portion 210 and a base portion 220. The main body portion 210 is provided with a plurality of the mold cavities; as shown in FIG. 3, the main body portion 210 is provided with the injecting inlet 212 at one side surface and the exhaust port 211 at the other side surface; and the exhaust surface is formed by a surface provided with the exhaust port 211. Due to differences between the methods for manufacturing the female mold, the female mold can be further provided with the base portion 220, the base portion having an inner surface covering over the exhaust surface and being internally provided with an exhaust hole 221. The exhaust hole 221 is in communication with the exhaust port 211 at an end and is open at an outer surface of the base portion 220 at the other end. The exhaust hole 221 has the same maximum radial size as that of the exhaust port 211, and a length greater than 0 µm but less than or equal to 500 µm. At this time, the gas-permeable membrane covers over the outer surface of the base portion to prevent the passage of liquid and allow the passage of gas. It can be understood that, if the female mold does not include the base portion, the gas-permeable membrane covers the exhaust surface for preventing the passage of liquid and allowing the passage of gas.

In some embodiments, the exhaust port 211 has a maximum radial size in the range of 0.1 µm to 100 µm. If the exhaust port is round in shape, the diameter is the maximum radial size; if the exhaust port is square in shape, the diagonal line length is the maximum radial size. The injecting inlet 212 has a maximum radial size in the range of 50 µm to 500 µm. The injecting inlet is preferably regular polygon or round in shape, wherein regular polygon can be square, regular hexagon, and the like. The diagonal line length or diameter is the maximum radial size. The female mold has a thickness from the injecting inlet side to an exhaust port side of the base portion, i.e. the overall thickness of the female mold, in the range of 50 µm to 3,000 µm.

In some embodiments, the gas-permeable membrane is made of a polytetrafluoroethylene film or an adhesive fiber membrane of polytetrafluoroethylene and polyester fiber, wherein the polytetrafluoroethylene film further includes an expanded polytetrafluoroethylene film. The gas-permeable membrane is preferably an adhesive film of expanded polytetrafluoroethylene and expanded polyester fiber. In order to achieve a better gas exhaust effect, the gas-permeable membrane has an effect of waterproofness and gas permeability of 120 to 1,500 $cm^3(cm^2/h)@0.1$ bar under a positive pressure in the range of 0.001 Mpa to 0.5 Mpa, or a negative pressure in the range of −0.5 Mpa to −0.001 Mpa. Generally, the gas-permeable membrane, which has a thickness in the range of 50-2,000 μm and a micropore having a pore size of 0.05 μm to 0.5 μm provided thereon, is selected.

Figure 4:
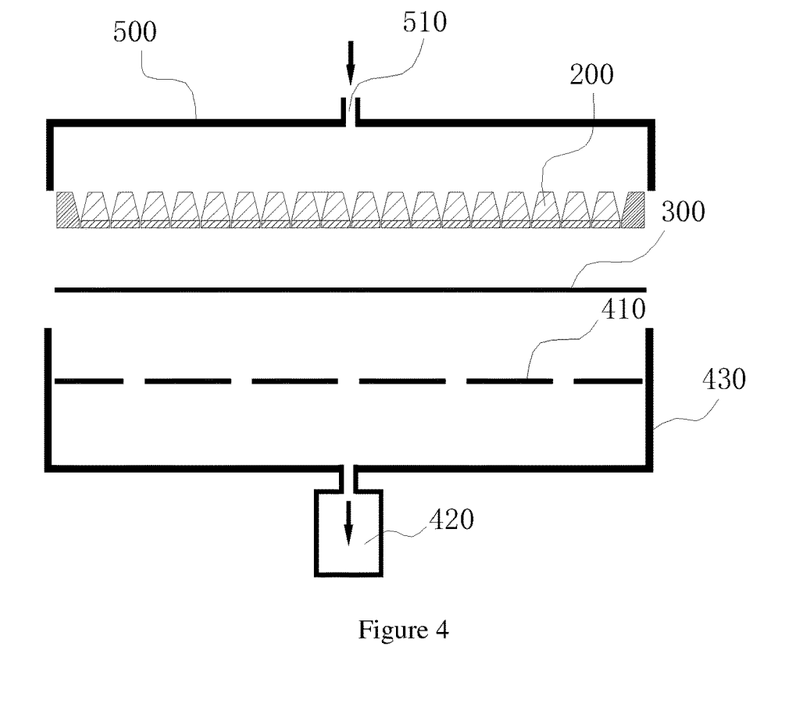
FIG. 4 is a schematic view of a mold set used in a specific embodiment.
Figure 5:
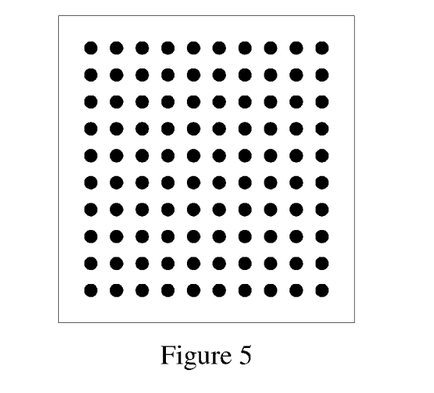
FIG. 5 is a top schematic view of a supporting plate according to a specific embodiment.

In some embodiments, in order to facilitate the operation, as shown in FIG. 4, the mold further comprises a supporting plate 410, a vacuum system, and a pressurizing system; as shown in FIG. 5, the supporting plate 410 is besprinkled with through-holes and arranged below the gas-permeable membrane 300 so as to support the female mold 200 and the gas-permeable membrane 300. The vacuum system comprises a vacuum pump 420 and a first frame body 430. The first frame body 430 is disposed along an edge of the supporting plate 410. Meanwhile, a receiving chamber for receiving the female mold 200 and the gas-permeable membrane 300 is formed on one side of the supporting plate 410, and a sealed hollow chamber is formed on the other side of the supporting plate 410. The sealed hollow chamber is in communication with the vacuum pump 420. The pressurizing system comprises a second frame body 500. The second frame body 500 is matched with the first frame body 430, so that the female mold 200 and the gas-permeable membrane 300 are sealed in the receiving chamber, and a liquid loading port 510 for increasing a pressure and loading a liquid is provided on the second frame body 500.

Example 1

A method for manufacturing a microneedle chip comprises the following steps:

1. Manufacture of the Male Mold

By using MEMS (Micro-Electro-Mechanical System) technology, a male mold with a conical needle body model on the surface was formed by processing brass as raw material.

In addition to brass, the male mold was also made of at least one of stainless steel, aluminum, a titanium alloy, nickel, palladium, silicon, and silicon dioxide. It was only necessary to select a female mold that is made of hard material and can cooperate with the female mold liquid solution to make mold cavities with good shape.

The male mold can also be made by methods, such as ion etching, laser cutting, chemical etching, X-ray lithography micro-electro-mechanical systems, or UV lithography micro-electro-mechanical systems, and the like. It was only necessary to make a positive model with a precise shape.

Figure 6:
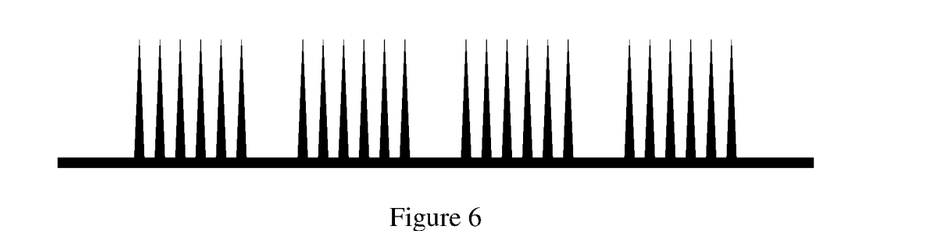
FIG. 6 is a schematic view of a male mold according to Example 1.

As shown in FIG. 6, the male mold was provided with an array of microneedle chip needle body model with 10×10 rows (100 pieces) and a height of 550 μm. In the array of microneedle chip needle body model, the needle body model has a bottom diameter of 150 μm and a needle spacing of 150 μm.

2. Manufacture of the Female Mold

The pre-mixed and degassed Sylgard 184 silicone elastomer was taken as a female mold liquid solution and injected into the above male mold. The male mold was placed on a horizontal plane so that the needle tip of the male mold was pierced through a liquid surface of the female mold liquid solution. The male mold was left at 100° C. for 20 mins, and the female mold liquid solution was cured and demoulded to form a female mold of 5.0 cm×5.0 cm. The female mold was besprinkled with mold cavities that were sieve-like in shape and matched with the shape of the needle bodies of the microneedle chip. Meanwhile, due to the needle tip of the male mold being pierced through the liquid surface, the mold cavity of the female mold had an exhaust port at the needle tip end and in communication with the outer surface of the female mold. The exhaust port was round in shape and had a pore size of 15 μm.

3. Microinjection (1). Preparation of Solution

Dextran 40000, bovine serum albumin (BSA), carboxymethyl cellulose (CMC), and water for injection were mixed in a mass fraction ratio of 0.8:0.2:0.2:4.0, swelled until no significant precipitate left and used as the fluidized needle body liquid.

The fluidized needle body liquid had a viscosity of 3765 cP.

(2). Injection

A mold set as shown in FIG. 4 was used. The mold set further comprised a supporting plate 410, a vacuum system, and a pressurizing system. As shown in FIG. 5, the supporting plate 410 was besprinkled with through-holes and arranged below the gas-permeable membrane 300 so as to support the female mold 200 and the gas-permeable membrane 300. The vacuum system comprised a vacuum pump 420 and a first frame body 430. The first frame body 430 was disposed along an edge of the supporting plate 410. Meanwhile, a receiving chamber for receiving the female mold 200 and the gas-permeable membrane 300 was formed on one side of the supporting plate 410, and a sealed hollow chamber was formed on the other side of the supporting plate 410. The sealed hollow chamber was in communication with the vacuum pump 420. The pressurizing system comprised a second frame body 500. The second frame body 500 was matched with the first frame body 430, so that the female mold 200 and the gas-permeable membrane 300 were sealed in the receiving chamber, and a liquid loading port 510 for increasing a pressure and loading a liquid was provided on the second frame body 500.

The above female mold was placed on a gas-permeable membrane made of a 4.0 cm×4.0 cm adhesive film of expanded polytetrafluoroethylene and polyester fiber, and the female mold and the gas-permeable membrane were placed as a whole on the supporting plate.

Figure 7:
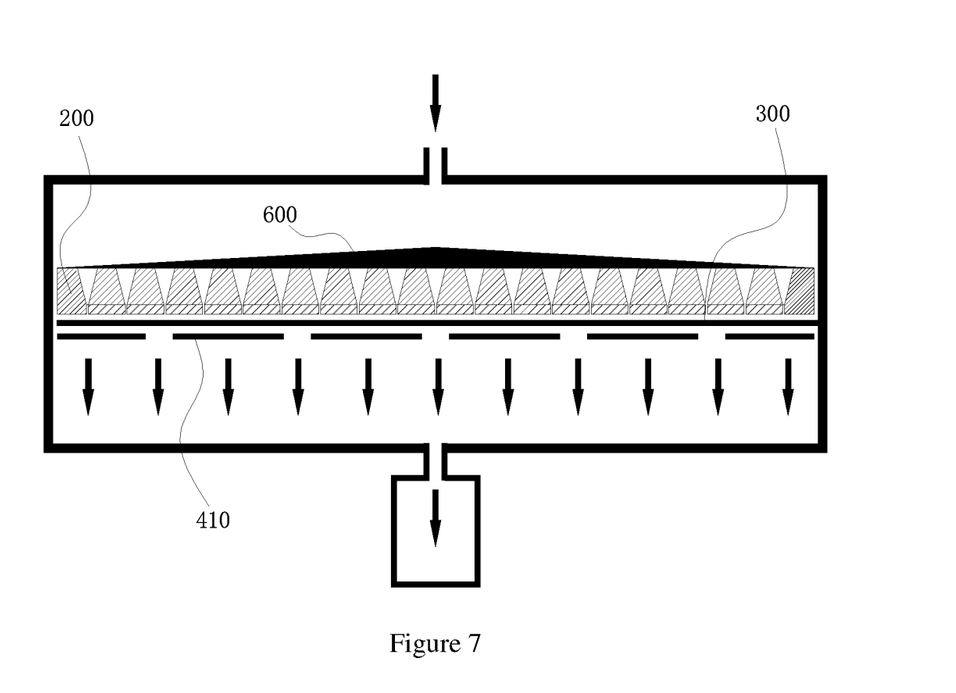
FIG. 7 is a schematic view of an injection process according to Example 1.
Figure 8:
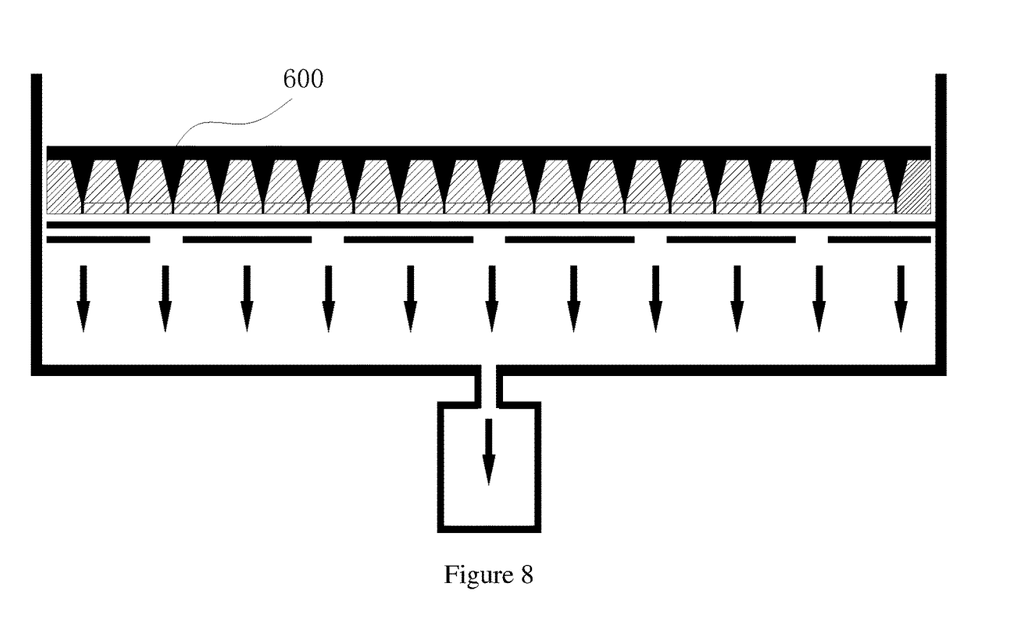
FIG. 8 is a schematic view of the fluidized needle body liquid fully injecting into the mold cavities of the female mold according to Example 1.

Firstly, an appropriate amount of the above fluidized needle body liquid was sucked up and covered over a surface of the female mold to ensure that all the micropores of the mold cavities in the female mold were covered. As shown in FIG. 7, the female mold was covered and sealed with the second frame body; a pressure of 0.04 Mpa was applied from the liquid loading port in the upper portion, so that the fluidized needle body liquid was injected into the mold cavities matched with the shape of the needle bodies of the microneedle chip, as shown in FIG. 8.

4. Coating the Needle Base (1). Preparation of Solution

Polyvinylpyrrolidone (PVP) K30, copolymer Gantrez AN-139, glycerol, and ethanol solution having a volume percent of 50% were mixed in a mass fraction ratio of 1:3:0.5:10, uniformly swelled and used as a needle base material.

(2). Coating

Figure 9:
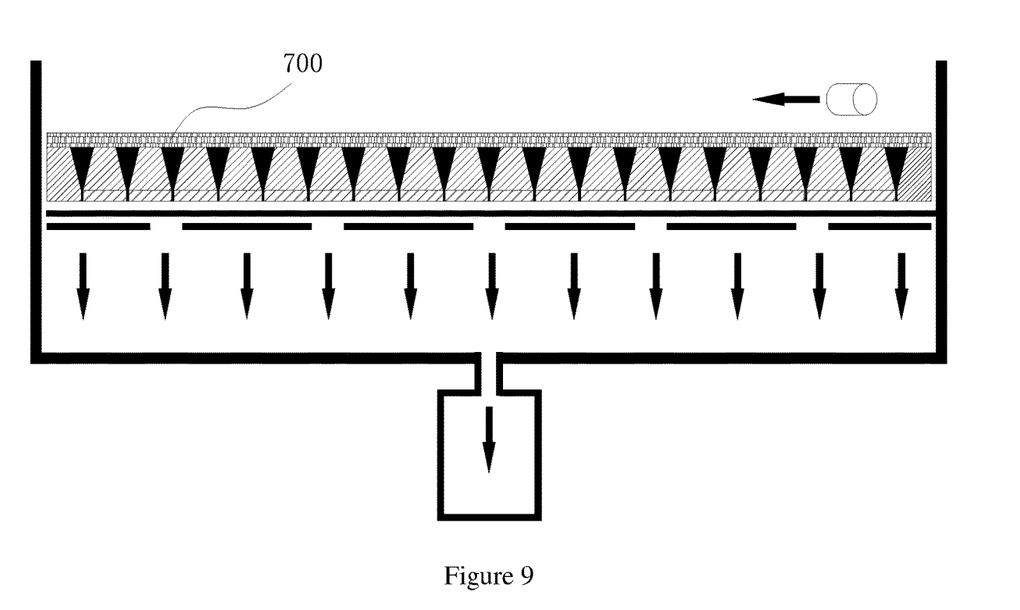
FIG. 9 is a schematic view of coating with a needle base material according to Example 1.

Excess needle body liquid was scraped away, and a solution of the above needle base material was coated by means of coating on the surface of the female mold that had been injected with the needle body liquid, as shown in FIG. 9.

5. Curing and Demoulding

Figure 10:
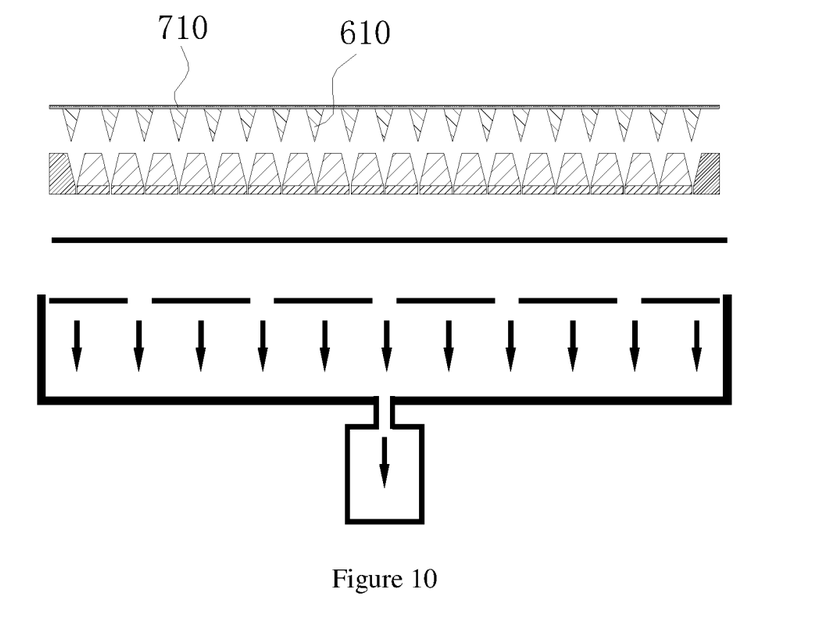
FIG. 10 is a schematic view of a demoulding process according to Example 1.

The above fluidized needle body liquid and the solution of the needle base material solution, after being cured and dried, was demoulded to give a blank microneedle chip without a drug, as shown in FIG. 10. The microneedle chip comprised a needle base layer 710 and a needle body 610. The microneedle chip obtained in this example, due to a good microinjection effect and no air embolism formation during the microinjection, was less prone to phenomenon of needle breakage or deficiency, and has a better uniformity and quality than those manufactured by conventional methods.

Example 2

A method for manufacturing a microneedle chip comprises the following steps:

1. Manufacture of the Male Mold

By using MEMS (Micro-Electro-Mechanical System) technology, a male mold with a conical needle body model on the surface was formed by processing brass as raw material. The male mold was provided with an array of microneedle chip needle body model with 10×10 rows (100 pieces) and a height of 950 μm. In the array of microneedle chip needle body model, the needle body model has a bottom diameter of 200 μm and a needle spacing of 300 μm.

2. Manufacture of the Female Mold

The pre-mixed and degassed Sylgard 184 silicone elastomer was taken as a female mold liquid solution and injected into the above male mold. The male mold was placed on a horizontal plane so that the height, at which the needle tip of the male mold was submerged in the female mold liquid solution, is 200 μm. The male mold was left at 60° C. for 4 hours, and the female mold liquid solution was cured and demoulded to form a female mold of 5.0 cm×5.0 cm. Then an exhaust hole was made by perforating at a position corresponding to the needle hole at the other side of the female mold with a UV laser. Furthermore, the exhaust hole penetrated into the mold cavity and formed an exhaust port in the mold cavity matched with the shape of the needle body. The exhaust port was round in shape, and had a pore size of 30 μm. Finally, a female mold having a thick of 1150 μm was obtained. The female mold was besprinkled with mold cavities that were sieve-like in shape and matched with the shape of the needle bodies of the microneedle chip. The exhaust port was round in shape and had a pore size of 30 μm, and the exhaust hole had a length of 200 μm.

3. Microinjection

(1). Preparation of Solution

Dextran 40000, bovine serum albumin (BSA), polyethylene glycol (PEG) 6000, salmon calcitonin (sCT), and water for injection were mixed in a mass fraction ratio of 1.0:0.3:0.4:0.1:4.0, swelled until no significant precipitate left and used as the fluidized needle body liquid.

The fluidized needle body liquid had a viscosity of 4872 cP.

(2). Injection

Injection was carried out by using the mold set of the Example 1.

The above female mold was placed on a gas-permeable membrane made of a 4.0 cm×4.0 cm adhesive film of polytetrafluoroethylene and polyester fiber, and the female mold and the gas-permeable membrane were placed as a whole on the supporting plate.

Firstly, an appropriate amount of the above fluidized needle body liquid was sucked up and covered over a surface of the female mold to ensure that all the micropores of the mold cavities in the female mold were covered. The female mold was covered and sealed with the second frame body; a pressure of 0.02 Mpa was applied from the liquid loading port in the upper portion, so that the fluidized needle body liquid was injected into the mold cavities matched with the shape of the needle bodies of the microneedle chip.

4. Coating the Needle Base

(1). Preparation of Solution

Polyvinylpyrrolidone (PVP) K30, copolymer Gantrez AN-139, and ethanol solution having a volume percent of 50% were mixed in a mass fraction ratio of 1:3:10, uniformly swelled and used as a needle base material.

(2). Coating

Excess needle body liquid was scraped away, and a solution of the above needle base material was coated by means of coating on the surface of the female mold that had been injected with the needle body liquid.

5. Curing and Demoulding

The above fluidized needle body liquid and the solution of the needle base material solution, after being cured and dried, was demoulded to give a microneedle chip containing salmon calcitonin. The microneedle chip was less prone to phenomenon of needle breakage or deficiency, and has a better uniformity and quality.

Example 3

A method for manufacturing a microneedle chip comprises the following steps:

1. Manufacturing of the Male Mold

By using MEMS (Micro-Electro-Mechanical System) technology, a male mold with a conical needle body model on the surface was formed by processing brass as raw material. The male mold was provided with an array of microneedle chip needle body model with 10×20 rows (100 pieces) and a height of 250 μm. In the array of microneedle chip needle body model, the needle body model has a bottom diameter of 100 μm and a needle spacing of 100 μm.

2. Manufacturing of the Female Mold

The pre-mixed and degassed SILASTIC MDX4-4210 silicone elastomer was taken as a female mold liquid solution and injected into the above male mold. The male mold was placed on a horizontal plane so that the needle tip of the male mold was pierced through a liquid surface of the female mold liquid solution. The male mold was left at room temperature for 24 hours, and the female mold liquid solution was cured and demoulded to form a female mold of 5.0 cm×5.0 cm. The female mold was besprinkled with mold cavities that were sieve-like in shape and matched with the shape of the needle bodies of the microneedle chip. Meanwhile, since the needle tip of the male mold was pierced through the liquid surface, the mold cavities of the female mold had an exhaust port at the needle tip end and in communication with an outer surface of the female mold. The exhaust port was round in shape and had a pore size of 25 μm.

3. Microinjection (1). Manufacturing of Solution

Dextran 40000, bovine serum albumin (BSA), polyethylene glycol (PEG) 4000, salmon calcitonin (sCT), and water for injection were mixed in a mass fraction ratio of 0.8:0.2:0.4:0.1:3.5, swelled uniformly and used as the fluidized needle body liquid.

The fluidized needle body liquid had a viscosity of 4069 cP.

2. Injection

Injection was carried out by using the mold set of the Example 1.

The above female mold was placed on a gas-permeable membrane made of 4.0 cm×4.0 cm polytetrafluoroethylene film, and the female mold and the gas-permeable membrane were placed as a whole on the supporting plate.

Firstly, an appropriate amount of the above fluidized needle body liquid was sucked up and covered over a surface of the female mold to ensure that all the micropores of the mold cavities in the female mold were covered. The female mold was covered and sealed with the second frame body. A negative pressure of −0.03 Mpa was made by vacuumizing from the lower portion, so that the fluidized needle body liquid was injected into the mold cavities matched with the shape of the needle bodies of the microneedle chip.

4. Coating the Needle Base (1). Manufacturing of Solution

Polyvinylpyrrolidone (PVP) K90, hyaluronic acid, copolymer Gantrez S97 BF and ethanol solution having a volume percent of 50% were mixed in a mass fraction ratio of 2:2:1:9, uniformly swelled and used as a needle base material.

(2). Coating

Excess needle body liquid was scraped away, and a solution of the above needle base material was coated by means of coating on the surface of the female mold that had been injected with the needle body liquid.

5. Curing and Demoulding

The above fluidized needle body liquid and the solution of the needle base material solution, after being cured and dried, was demoulded to give a microneedle chip containing salmon calcitonin. The microneedle chip was less prone to phenomenon of needle breakage or deficiency, and has a better uniformity and quality.

Example 4

A method for manufacturing a microneedle chip comprises the following steps:

1. Manufacturing of the Male Mold

By using MEMS (Micro-Electro-Mechanical System) technology, a male mold with a conical needle body model on the surface was formed by processing brass as raw material. The male mold was provided with an array of microneedle chip needle body model with 10×15 rows (150 pieces) and a height of 750 μm. In the array of microneedle chip needle body model, the needle body model has a bottom diameter of 200 μm and a needle spacing of 200 μm.

2. Manufacturing of the Female Mold

The pre-mixed and degassed Sylgard 184 silicone elastomer was taken as a female mold liquid solution and injected into the above male mold. The male mold was placed on a horizontal plane so that the needle tip of the male mold was pierced through a liquid surface of the female mold liquid solution. The male mold was left at 120° C. for 15 mins, and the female mold liquid solution was cured and demoulded to form a female mold of 5.0 cm×5.0 cm. The female mold was besprinkled with mold cavities that were sieve-like in shape and matched with the shape of the needle bodies of the microneedle chip. Meanwhile, since the needle tip of the male mold was pierced through the liquid surface, the mold cavities of the female mold had an exhaust port at the needle tip end and in communication with an outer surface of the female mold. The exhaust port was round in shape and had a pore size of 15 μm.

3. Microinjection (1). Manufacturing of Solution

Dextran 60000, hyaluronic acid, Thymopentin (Tp5), and water for injection were mixed in a mass fraction ratio of 0.8:0.4:0.01:3.5, swelled until no significant precipitate left and used as the fluidized needle body liquid.

The fluidized needle body liquid had a viscosity of 2193 cP.

2. Injection

Injection was carried out by using the mold set of the Example 1.

The above female mold was placed on a gas-permeable membrane made of a 4.0 cm×4.0 cm adhesive film of polytetrafluoroethylene and polyester fiber, and the female mold and the gas-permeable membrane were placed as a whole on the supporting plate.

Firstly, an appropriate amount of the above fluidized needle body liquid was sucked up and covered over a surface of the female mold to ensure that all the micropores of the mold cavities in the female mold were covered. The female mold was covered and sealed with the second frame body. Two approaches was combined, including increasing a pressure of 0.1 Mpa from the upper portion and making a negative pressure of −0.1 Mpa by vacuumizing from the lower portion, so that the fluidized needle body liquid was injected into the mold cavities matched with the shape of the needle bodies of the microneedle chip.

4. Coating the Needle Base (1). Manufacturing of Solution

Polyvinylpyrrolidone (PVP) K90, glycerol, and anhydrous ethanol were mixed in a mass fraction ratio of 1:0.1:2.5, uniformly swelled and used as a needle base material.

(2). Coating

Excess needle body liquid was scraped away, and a solution of the above needle base material was coated by means of coating on the surface of the female mold that had been injected with the needle body liquid.

5. Curing and Demoulding

The above fluidized needle body liquid and the solution of the needle base material solution, after being cured and dried, was demoulded to give a microneedle chip containing thymopentin. The microneedle chip was less prone to phenomenon of needle breakage or deficiency, and has a better uniformity and quality.

Example 5

A method for manufacturing a microneedle chip comprises the following steps:

1. Manufacturing of the Male Mold

By using chemical etching technology, a male mold with a conical needle body model on the surface was formed by processing silicon oxide as raw material. The male mold was provided with an array of microneedle chip needle body model with 10×20 rows (200 pieces) and a height of 550 μm. In the array of microneedle chip needle body model, the needle body model has a bottom diameter of 180 μm and a needle spacing of 100 μm.

2. Manufacturing of the Female Mold

The pre-mixed and degassed Sylgard 184 silicone elastomer was taken as a female mold liquid solution and injected into the above male mold. The male mold was placed on a horizontal plane so that the needle tip of the male mold was pierced through a liquid surface of the female mold liquid solution. The male mold was left at 120° C. for 20 mins, and the female mold liquid solution was cured and demoulded to form a female mold of 5.0 cm×5.0 cm. The female mold was besprinkled with mold cavities that were sieve-like in shape and matched with the shape of the needle bodies of the microneedle chip. Meanwhile, since the needle tip of the male mold was pierced through the liquid surface, the mold cavities of the female mold had an exhaust port at the needle tip end and in communication with an outer surface of the female mold. The exhaust port was round in shape and had a pore size of 20 μm.

3. Microinjection (1). Manufacturing of Solution

Dextran 40000, polyethylene glycol (PEG) 4000, chondroitin sulfate, salmon calcitonin, and water for injection were mixed in a mass fraction ratio of 1.0:0.5:0.2:0.1:4.0, swelled until no significant precipitate left and used as the fluidized needle body liquid.

The fluidized needle body liquid had a viscosity of 8178 cP.

2. Injection

Injection was carried out by using the mold set of the Example 1.

The above female mold was placed on a gas-permeable membrane made of a 4.0 cm×4.0 cm adhesive film of polytetrafluoroethylene and polyester fiber, and the female mold and the gas-permeable membrane were placed as a whole on the supporting plate.

Firstly, an appropriate amount of the above fluidized needle body liquid was sucked up and covered over a surface of the female mold to ensure that all the micropores of the mold cavities in the female mold were covered. The female mold was covered and sealed with the second frame body. Two approaches was combined, including increasing a pressure of 0.01 Mpa from the upper portion and making a negative pressure of −0.05 Mpa by vacuumizing from the lower portion, so that the fluidized needle body liquid was injected into the mold cavities matched with the shape of the needle bodies of the microneedle chip.

4. Coating the Needle Base (1). Manufacturing of Solution

Polyvinylpyrrolidone (PVP) K30, glycerol, and ethanol aqueous solution having a volume percent of 60% were mixed in a mass fraction ratio of 5:0.5:8, uniformly swelled and used as a needle base material.

(2). Coating

Excess needle body liquid was scraped away, and a solution of the above needle base material was coated by means of coating on the surface of the female mold that had been injected with the needle body liquid.

5. Curing and Demoulding

The above fluidized needle body liquid and the solution of the needle base material solution, after being cured and dried, was demoulded to give a microneedle chip containing salmon calcitonin. The microneedle chip was less prone to phenomenon of needle breakage or deficiency, and has a better uniformity and quality.

The technical features in the above-described embodiments may be combined arbitrarily. For clarity of description, not all the possible combinations of the technical features in the above embodiments are described. However, as long as no contradiction exists between the combination of these technical features, it should be considered as being within the scope recorded in this Specification.

The above-mentioned examples merely represent several embodiments of the present disclosure, and are described in a specific and detailed way, but it should not be construed as limiting the scope of the present disclosure. It should be noted that, for those skilled in the art, several variations and improvements may be made without departing from the concept of the present disclosure, and these are all within the protection scope of the present disclosure. Therefore, the scope of protection of the present disclosure shall be subject to the appended claims.

What is claimed is:

1. A method for manufacturing a microneedle chip, the method comprising:
    placing a female mold with a gas-permeable membrane on a supporting plate besprinkled with through-holes, wherein the female mold is provided with a plurality of mold cavities matched with a shape of a needle body of the microneedle chip, each of the plurality of mold cavities is provided with an injecting inlet and an exhaust port, the plurality of mold cavities are arranged in a same direction to form an array of mold cavities, wherein the injecting inlet is open at one side surface of the female mold and located at a needle base end of the plurality of mold cavities, the exhaust port is open at the other side surface of the female mold and located at a needle tip end of the plurality of mold cavities, and a surface of the female mold having a plurality of the exhaust ports forms an exhaust surface; the gas-permeable membrane covers the exhaust surface, wherein the gas-permeable membrane is waterproof and has a gas permeability in a range of 12,000 to 150,000 cm3/(cm2*h*MPa) under a positive pressure in a range of 0.001 MPa to 0.5 MPa, or under a negative pressure in a range of −0.5 MPa to −0.001 MPa;
    placing the female mold, the gas-permeable membrane and the supporting plate in a chamber enclosed by a vacuum system and a pressurizing system, wherein the vacuum system comprises a vacuum pump and a first frame body that is disposed along an edge of the supporting plate, a receiving chamber for receiving the female mold and the gas-permeable membrane is formed on one side of the supporting plate, and a sealed hollow chamber that is in communication with the vacuum pump is formed on the other side of the supporting plate; and the pressurizing system comprises a second frame body that is matched with the first frame body so as to seal the female mold and the gas-permeable membrane in the receiving chamber, and a liquid loading port for applying pressure and loading liquid is disposed on the second frame body;
    injecting a fluidized needle body liquid containing a bioactive component from the liquid loading port into the female mold;
    allowing gas to pass through the gas-permeable membrane and the fluidized needle body liquid to be retained within the plurality of mold cavities by applying a positive pressure at a injecting side of the female mold to promote the injection of the fluidized needle body liquid into the mold cavities; and/or by vacuumizing at an exhaust port side of the female mold to form a negative pressure to promote the injection of the fluidized needle body liquid into the mold cavities; and demolding after the fluidized needle body liquid is cured to form the microneedle chip.

2. The method of claim 1, wherein the positive pressure applied at the injecting side of the female mold has an intensity of pressure in the range of 0.001 MPa to 0.9 MPa, and the negative pressure formed by vacuumizing at the exhaust port side of the female mold has an intensity of pressure in the range of −0.9 MPa to −0.001 MPa.

3. The method of claim 1, wherein the fluidized needle body liquid has a viscosity in a range of 100 cps to 60,000 cps.

4. The method of claim 3, wherein the fluidized needle body liquid has a viscosity in the range of 2,000 cps to 40,000 cps.

5. The method of claim 1, wherein the female mold includes a main body portion and a base portion; wherein the main body portion is provided with the plurality of the mold cavities, the injecting inlet at one side surface and the exhaust port at the other side surface, and the exhaust surface is formed by a surface provided with the exhaust port;
    the base portion has an inner surface covering over the exhaust surface and is internally provided with an exhaust hole, the exhaust hole in communication with the exhaust port at an end and open at an outer surface of the base portion at the other end, and having the same maximum radial size as that of the exhaust port and a length greater than 0 μm but less than or equal to 500 μm; and wherein the gas-permeable membrane covers over the outer surface of the base portion.

6. The method of claim 5, wherein the female mold has a thickness from an injecting inlet side to an outer surface side of the base portion in the range of 50 μm to 3,000 μm.

7. The method of claim 1, wherein the exhaust port has a maximum radial size in the range of 0.1 μm to 100 μm.

8. The method of claim 1, wherein the gas-permeable membrane is made of a polytetrafluoroethylene film or an adhesive fiber membrane of polytetrafluoroethylene and polyester fiber.

9. The method of claim 1, wherein the female mold is made of polydimethylsiloxane.

10. The method of claim 1, wherein after the fluidized needle body liquid is injected into the plurality of mold cavities of the female mold, a needle base material is coated on a needle base portion of the microneedle chip via a coating, and the fluidized needle body liquid and the needle base material, after being cured, are demolded to give the microneedle chip.

11. The method of claim 10, wherein the needle base material is at least one of polyvinylpyrrolidone K30, copolymer Gantrez AN-139, copolymer Gantrez S97 BF, or hyaluronic acid.

* * * * *